United States Patent [19]
Stevenson et al.

[11] Patent Number: 6,124,261
[45] Date of Patent: *Sep. 26, 2000

[54] NON-AQUEOUS POLAR APROTIC PEPTIDE FORMULATIONS

[75] Inventors: Cynthia L. Stevenson; Steven J. Prestrelski, both of Mountain View, Calif.

[73] Assignee: ALZA Corporation, Mt. View, Calif.

[*] Notice: This patent is subject to a terminal disclaimer.

[21] Appl. No.: 09/293,839

[22] Filed: Apr. 19, 1999

Related U.S. Application Data

[63] Continuation of application No. 08/874,233, Jun. 13, 1997.
[60] Provisional application No. 60/022,699, Jul. 3, 1996.

[51] Int. Cl.$^7$ .......................... A61K 38/00; A61K 38/24; C07K 5/00; C07K 7/00
[52] U.S. Cl. .............................. 514/12; 514/15; 530/313; 530/328; 424/600
[58] Field of Search ........................ 514/12, 15; 424/600; 530/313, 328

[56] References Cited

U.S. PATENT DOCUMENTS

| | | | |
|---|---|---|---|
| 3,914,412 | 10/1975 | Gendrich et al. | 424/177 |
| 4,547,370 | 10/1985 | Roeske | 514/15 |
| 4,661,472 | 4/1987 | Rivier et al. | 514/15 |
| 4,689,396 | 8/1987 | Roeske et al. | 530/313 |
| 4,851,385 | 7/1989 | Roeske | 514/15 |
| 5,034,229 | 7/1991 | Magruder et al. | 424/422 |
| 5,057,318 | 10/1991 | Magruder et al. | 424/438 |
| 5,110,596 | 5/1992 | Magruder et al. | 424/438 |
| 5,198,533 | 3/1993 | Schally et al. | 530/313 |
| 5,480,868 | 1/1996 | Kamei et al. | 514/15 |
| 5,932,547 | 8/1999 | Stevenson et al. | 514/15 |

FOREIGN PATENT DOCUMENTS

| | | | |
|---|---|---|---|
| 1098151 | 12/1964 | United Kingdom | A61K 3/00 |
| 2008403A | 11/1978 | United Kingdom | |
| 2119248A | 4/1983 | United Kingdom | |
| 2119248 | 11/1983 | United Kingdom | A61K 37/26 |
| WO92/20711 | 11/1992 | WIPO | |
| WO94/19020 | 9/1994 | WIPO | |
| WO95/00168 | 1/1995 | WIPO | |
| WO95/04540 | 2/1995 | WIPO | |
| WO97/27840 | 8/1997 | WIPO | |

OTHER PUBLICATIONS

Factrel (gonadorelin HCl for subcutaneous or IV injection), *Physician's Desk Ref.*, 50th Ed., pp. 2877–2878 (1996).
Fu Lu, et al., "Percutaneous Absorption Enhancement of Leuprolide", *Pharm. Res.*, 9/12, pp. 1575–1576 (1992).
Helm, et al., "Stability of Gonadorelin and Triptorelin in Aqueous Solution", *Pharm. Res.*, 7/12, pp. 1253–1256 (1990).
Johnson, et al., "Degradation of the LH–RH Analog Nafarelin Acetate in Aqueous Solution", *Intl. J. Pharm.*, 31, pp. 125–129 (1986).
Lupron (leuprolide acetate for subcutaneous injection), *Physician's Desk Ref.*, 50th Ed., pp. 2555–2556 (1996).
Lupron Depot (leuprolide acetate for depot suspension), *Physician's Desk Ref.*, 50th Ed., pp. 2556–2562 (1996).
Lutrepulse (gonadorelin acetate for IV injection), *Physician's Desk Ref.*, 50th Ed., pp. 980–982 (1996).
Okada, et al., "New Degradation Product of Des–Gly$^{10}$–NH$_2$–LH–RH–Ethylamide (Fertirelin) in Aqueous Solution", *J. Pharm. Sci.*, 80/2, pp. 167–170 (1991).
Okada, et al., "Preparation of Three–Month Depot Injectable Microspheres of Leuprorelin Acetate Using Biodegradable Polymers", *Pharm. Res.*, 11/8, pp. 1143–1147 (1994).
Oyler, et al., "Characterization of the Solution Degradation Products of Histrelin, a Gonadotropin Releasing Hormone (LH/RH) Agonist", *J. Pharm. Sci.*, 80/3, pp. 271–275 (1991).
Powell, et al., "Parenteral Peptide Formulations: Chemical and Physical Properties of Native Luteinizing Hormone–Releasing Hormone (LHRH) and Hydrophobic Analogues in Aqueous Solution", *Pharm. Res.*, 8/10, pp. 1258–1263 (1991).
Powell, et al., "Peptide Liquid Crystals: Inverse Correlation of Kinetic Formation and Thermodynamic Stability in Aqueous Solution", *Pharm. Res.*, 11/9, pp. 1352–1354 (1994).
Powers, et al., "Solution Behavior of Leuprolide Acetate, an LHRH Agonist, as Determined by Circular Dichroism Spectroscopy", *Intl. J. Pharm.*, 108, pp. 49–55 (1994).
Shi, et al., "Long–Term Stability of Aqueous Solutions of Luteinizing Hormone–Releasing Hormone Assessed by an In–Vitro Bioassay and Liquid Chromatography", *J. Pharm. Sci.*, 73/6, pp. 819–821 (1984).
Toguchi, "Pharmaceutical Manipulation of Leuprorelin Acetate to Improve Clinical Performance", *J. Intl. Med. Res.*, 18, pp. 35–41 (1990).
Zoladex (goserelin acetate implant), *Physician's Desk Ref.*, 50th Ed., pp. 2858–2861 (1996).

*Primary Examiner*—Avis M. Davenport
*Attorney, Agent, or Firm*—Mary Ann Dillahunty; Steven F. Stone; Pauline A. Clarke

[57] ABSTRACT

This invention relates to stable non-aqueous polar aprotic formulations of peptide compounds. These stable formulations comprise peptide in non-aqueous polar aprotic solvent. They may be stored at elevated temperatures for long periods of time and are especially useful in implantable delivery devices for long term delivery of drug.

41 Claims, 8 Drawing Sheets

NON-AQUEOUS POLAR APROTIC PEPTIDE FORMULATIONS

CROSS-REFERENCE TO RELATED APPLICATIONS

This application is a continuation, of application Ser. No. 08/874,233, filed Jun. 13, 1997.

This application claims priority under 35 U.S.C. 119(e) to U.S. application Ser. No. 60/022,699 filed Jul. 3, 1996, the disclosure of which is incorporated herein by reference.

FIELD OF THE INVENTION

This invention relates to stable non-aqueous polar aprotic formulations of peptide compounds and more particularly to formulations of peptide compounds at high concentrations.

BACKGROUND OF THE INVENTION

References:

The following references are referred to by numbers in brackets ([ ]) at the relevant portion of the specification.
1. Zoladex (goserelin acetate implant), Physician's Desk Reference, 50th Edition, pages 2858–2861 (1996).
2. U.S. Pat. No. 3,914,412, issued Oct. 21, 1975.
3. U.S. Pat. No. 4,547,370, issued Oct. 15, 1985.
4. U.S. Pat. No. 4,661,472, issued Apr. 28, 1987.
5. U.S. Pat. No. 4,689,396, issued Aug. 25, 1987.
6. U.S. Pat. No. 4,851,385, issued Jul. 25, 1989.
7. U.S. Pat. No. 5,198,533, issued Mar. 30, 1993.
8. U.S. Pat. No. 5,480,868, issued Jan. 2, 1996.
9. WO92/2071 1, published Nov. 26, 1992.
10. WO95/00168, published Jan. 5, 1995.
11. WO95/04540, published Feb. 16, 1995.
12. "Stability of Gonadorelin and Triptorelin in Aqueous Solution", V. J. Helm, B. W. Muller, *Pharmaceutical Research*, 7/12, pages 1253–1256 (1990).
13. "New Degradation Product of Des-Gly$^{10}$-NH$_2$-LH-RH-Ethylamide (Fertirelin) in Aqueous Solution", J. Okada, T. Seo, F. Kasahara, K. Takeda, S. Kondo, *J. of Pharmaceutical Sciences*, 80/2, pages 167–170 (1991).
14. "Characterization of the Solution Degradation Product of Histrelin, a Gonadotropin Releasing Hormone (LHRH) Agonist", A. R. Oyler, R. E. Naldi, J. R. Lloyd, D. A. Graden, C. J. Shaw, M. L. Cotter, *J. of Pharmaceutical Sciences*, 80/3, pages 271–275 (1991).
15. "Parenteral Peptide Formulations: Chemical and Physical Properties of Native Luteinizing Hormone-Releasing Hormone (LHRH) and Hydrophobic Analogues in Aqueous Solution", M. F. Powell, L. M. Sanders, A. Rogerson, V. Si, *Pharmaceutical Research*, 8/10, pages 1258–1263 (1991).
16. "Degradation of the LHRH Analog Nafarelin Acetate in Aqueous Solution", D. M. Johnson, R. A. Pritchard, W. F. Taylor, D. Conley, G. Zuniga, K. G. McGreevy, *Intl. J. of Pharmaceutics*, 31, pages 125–129 (1986).
17. "Percutaneous Absorption Enhancement of Leuprolide", M. Y. Fu Lu, D. Lee, G. S. Rao, *Pharmaceutical Research*, 9/12, pages 1575–1576 (1992).
18. Lutrepulse (gonadorelin acetate for IV injection), Physician's Desk Reference, 50th Edition, pages 980–982 (1996).
19. Factrel (gonadorelin HCl for subcutaneous or IV injection), Physician's Desk Reference, 50th Edition, pages 2877–2878 (1996).
20. Lupron (leuprolide acetate for subcutaneous injection), Physician's Desk Reference, 50th Edition, pages 2555–2556 (1996).
21. Lupron depot (leuprolide acetate for depot suspension), Physician's Desk Reference, 50th Edition, pages 2556–2562 (1996).
22. "Pharmaceutical Manipulation of Leuprorelin Acetate to Improve Clinical Performance", H. Toguchi, *J. of Intl. Medical Research*, 18, pages 35–41 (1990).
23. "Long-Term Stability of Aqueous Solutions of Luteinizing Hormone-Releasing Hormone Assessed by an In-Vitro Bioassay and Liquid Chromatography", Y. F. Shi, R. J. Sherins, D. Brightwell, J. F. Gallelli, D. C. Chatterji, *J. of Pharmaceutical Sciences*, 73/6, pages 819–821 (1984).
24. "Peptide Liquid Crystals: Inverse Correlation of Kinetic Formation and Thermodynamic Stability in Aqueous Solution", M. F. Powell, J. Fleitman, L. M. Sanders, V. C. Si, *Pharmaceutical Research*, 11/9, pages 1352–1354 (1994).
25. "Solution Behavior of Leuprolide Acetate, an LHRH Agonist, as Determined by Circular Dichroism Spectroscopy", M. E. Powers, A. Adejei, M. Y. Fu Lu, M. C. Manning, *Intl. J. of Pharmaceutics*, 108, pages 49–55 (1994).
26. "Preparation of Three-Month Depot Injectable Microspheres of Leuprorelin Acetate Using Biodegradable Polymers", *Pharmaceutical Research*, 11/8, pages 1143–1147 (1994).

The disclosure of each of the above publications, patents or patent applications is hereby incorporated by reference in its entirety to the same extent as if the language of each individual publication, patent and patent application were specifically and individually incorporated by reference.

Luteinizing hormone-releasing hormone (LHRH), also known as gonadotropin releasing hormone (GnRH), is a decapeptide with the structure:

pGlu-His-Trp-Ser-Tyr-Gly-Leu-Arg-Pro-Gly-NH$_2$.

It is secreted by the hypothalamus and binds to receptors on the pituitary gland, releasing luteinizing hormone (LH) and follicle stimulating hormone (FSH). LH and FSH stimulate the gonads to synthesize steroid hormones. Numerous analogs of LHRH are known, including peptides related to LHRH which act as agonists and those which act as antagonists. [1–15] LHRH analogs are known to be useful for treating hormone-dependent diseases such as prostate cancer, benign prostatomegaly, endometriosis, hysteromyoma, metrofibroma, precocious puberty, or mammary cancer and as contraceptives. [8] Sustained release administration is preferred for both agonist LHRH-related compounds, which reduce the number of available receptors after repeated administration so that the production of steroid hormones is suppressed, and antagonist LHRH-related compounds, which must be continually administered for persistent inhibition of endogenous LHRH. [8]

The sustained parenteral delivery of drugs, especially peptide drugs, provides many advantages. The use of implantable devices for sustained delivery of a wide variety of drugs or other beneficial agents is well known in the art. Typical devices are described, for example, in U.S. Pat. Nos. 5,034,229; 5,057,318; and 5,110,596. The disclosure of each of these patents is incorporated herein by reference.

In general, oral bioavailability of peptides, including LHRH-related compounds, is low. [16–17]

Currently marketed formulations of LHRH, its analogs and related compounds which are used for parenteral injection are aqueous solutions which contain relatively low concentrations of LHRH-related compounds (0.05 to 5 mg/ml) and may also contain excipients such as mannitol or lactose. [18–20] Such formulations of LHRH-related compounds must either be stored refrigerated or may be stored at room temperature for short periods of time.

Available depot formulations of LHRH-related compounds administered for sustained release over a period of 1–3 months include a formulation comprised of 15% LHRH-related compound dispersed in a matrix of D,L-lactic and glycolic acids copolymer presented as a cylinder to be injected subcutaneously [1] and a formulation comprised of microparticles comprising a core of LHRH-related compound and gelatin surrounded by a shell of D,L-lactic and glycolic acids copolymer. These microparticles are suspended in a diluent for injection either subcutaneously or intramuscularly. [21, 26] These products must be stored at room temperature or lower. Aqueous formulations of LHRH-related compounds are known to exhibit both chemical and physical instability, as well as degradation after irradiation. [12–16, 22–25]

Formulations which have been shown to be stable ($t_{90}$ about five years) have been very low concentration (25 µg/ml) aqueous, buffered (10 mM, ionic strength of 0.15) solutions stored at temperatures no higher than room temperature (25° C.). [15]

There is a need for stable formulations of peptides.

SUMMARY OF THE INVENTION

The present invention provides stable non-aqueous formulations which are solutions of peptide compounds in polar aprotic solvents. In particular, the peptide compounds are formulated at concentrations of at least about 10%. These stable formulations may be stored at elevated temperatures (e.g., 37° C.) for long periods of time and are especially useful in implantable delivery devices for long term delivery (e.g., 1–12 months or longer) of drug.

In one aspect, the invention provides stable non-aqueous formulations of peptide compounds, said formulations comprising at least one peptide compound in at least one polar aprotic solvent. In a preferred embodiment, the formulation comprises at least about 10% (w/w) peptide compound.

In another aspect, the invention provides methods for preparing a stable non-aqueous formulation of a peptide compound, said methods comprising dissolving at least one peptide compound in at least one polar aprotic solvent. Preferred formulations comprise at least about 10% (w/w) peptide compound.

In yet a further aspect, the invention provides methods for treating a subject suffering from a condition which may be alleviated by administration of a peptide compound, said methods comprising administering to said subject an effective amount of a stable non-aqueous formulation comprising at least one peptide compound in at least one polar aprotic solvent.

BRIEF DESCRIPTION OF THE DRAWINGS

FIG. 2 shows the same sample as FIG. 1 injected by size exclusion chromatography (SEC). This figure shows that there is very little aggregation, and what aggregation there is is comprised of dimer and trimer products, with no higher order aggregation.

DETAILED DESCRIPTION OF THE INVENTION

The present invention is drawn to the unexpected discovery that dissolving peptide compounds in non-aqueous polar aprotic solvents results in stable formulations. Previously known formulations of peptide compounds, which are dilute buffered aqueous solutions containing excipients such as EDTA or ascorbic acid which must be stored at low temperatures (4–25° C.), form degradation products using degradation pathways such as acid/base catalyzed hydrolysis, deamidation, racemization and oxidation. In contrast, the presently claimed formulations stabilize peptide compounds at elevated temperatures (e.g., 37° C. to 80° C.) and at high concentrations (i.e., at least about 10%).

Standard peptide and protein formulations consist of dilute aqueous solutions. Drug stability is usually achieved by varying one or more of the following: pH, buffer type, ionic strength, excipients (EDTA, ascorbic acid, etc). For these formulations, degradation pathways requiring water (hydrolysis, deamidation, racemization) cannot be fully stabilized. In contrast, in the present invention, peptides formulated in non-aqueous solutions, such as dimethyl sulfoxide (DMSO) and dimethyl formamide (DMF), were shown to be chemically and physically more stable than those formulated in water. DMSO and DMF are considered polar aprotic solvents. Aprotic solvents would be expected to decrease the rate of degradation since they lack the ability to contribute protons to degradation reactions. Conversely, solvents that are more polar than water (for example, the dipole moment of water is 1.85, for DMF is 3.82, and for DMSO is 3.96) would be expected to increase the rate of degradation since they can assist in stabilizing the rate determining step and increasing the rate of degradation. However, we discovered that the overall effect of polar aprotic solvents was generally to stabilize solutions of peptides.

The invention consists of using non-aqueous, aprotic solvents such as DMSO or DMF to stabilize peptide formulations against both chemical and physical degradation. The discovery consists of the realization that use of DMSO or DMF improves the overall stability of peptides in a wide range of formulation conditions, including high concentrations and elevated temperatures, thus making possible the delivery of peptides in long term implantable devices that would not otherwise be feasible.

A. Definitions:

As used herein, the following terms have the following meanings:

The term "chemical stability" means that an acceptable percentage of degradation products produced by chemical pathways such as oxidation or hydrolysis is formed. In particular, a formulation is considered chemically stable if no more than about 20% breakdown products are formed after two months at 37° C.

The term "physical stability" means that an acceptable percentage of aggregates (e.g., dimers, trimers and larger forms) is formed. In particular, a formulation is considered physically stable if no more that about 15% aggregates are formed after two months at 37° C.

The term "stable formulation" means that at least about 65% chemically and physically stable peptide compound remains after two months at 37° C. (or equivalent conditions at an elevated temperature). Particularly preferred formulations are those which retain at least about 80% chemically and physically stable peptide under these conditions. Especially preferred stable formulations are those which do not exhibit degradation after sterilizing irradiation (e.g., gamma, beta or electron beam).

The terms "peptide" and/or "peptide compound" mean polymers of up to about 50 amino acid residues bound together by amide (CONH) linkages. Analogs, derivatives, agonists, antagonists and pharmaceutically acceptable salts of any of these are included in these terms. The terms also include peptides and/or peptide compounds which have D-amino acids, modified, derivatized or non-naturally occurring amino acids in the D- or L- configuration and/or peptomimetic units as part of their structure.

The term "LHRH-related compound" means luteinizing hormone releasing hormone (LHRH) and its analogs and pharmaceutically acceptable salts. Octa-, nona- and decapeptide LHRH agonists and antagonists are included in the term LHRH-related compounds, as is native LHRH. Particularly preferred LHRH-related compounds include LHRH, leuprolide, goserelin, nafarelin, and other known active agonists and antagonists. [1–21]

The term "high concentration" means at least about 10% (w/w) and up to the maximum solubility of the particular peptide.

The term "excipient" means a more or less inert substance in a formulation which is added as a diluent or vehicle or to give form or consistency. Excipients are distinguished from solvents such as EtOH, which are used to dissolve drugs in formulations, and from non-ionic surfactants such as Tween 20, which are used to solubilize drugs in formulations, and from preservatives such as benzyl alcohols or methyl or propyl parabens, which are used to prevent or inhibit microbial growth.

The term "polar aprotic solvent" means a polar solvent which does not contain acidic hydrogen and does not act as a hydrogen bond donor. Examples of polar aprotic solvents are dimethylsulfoxide (DMSO), dimethylformamide (DMF), hexamethylphosphorotriamide (HMPT), and n-methyl pyrrolidone.

The term "non-aqueous protic solvent" means a non-polar solvent which contains hydrogen attached to oxygen or nitrogen so that it is able to form hydrogen bonds or donate a proton. Examples of apolar protic solvents are polyethylene glycols (PEGs), propylene glycol (PG), polyvinylpyrrolidone (PVP), methoxypropylene glycol (MPEG), glycerol and glycofurol.

B. Preparation of Formulations:

The present invention is drawn to non-aqueous formulations of peptide compounds in polar aprotic solvent which are stable for prolonged periods of time at elevated temperatures. Standard dilute aqueous peptide and protein formulations require manipulation of buffer type, ionic strength, pH and excipients (e.g., EDTA and ascorbic acid) to achieve stability. In contrast, the claimed formulations achieve stabilization of peptide compounds by the use of non-aqueous polar aprotic solvents. In particular, stability of high concentrations (at least about 10%, w/w) of compound has been provided by the formulations of the present invention.

Examples of peptides and peptide compounds which may be formulated using the present invention include those peptides which have biological activity or which may be used to treat a disease or other pathological condition. They include, but are not limited to adrenocorticotropic hormone, angiotensin I and II, atrial natriuretic peptide, bombesin, bradykinin, calcitonin, cerebellin, dynorphin A, alpha and beta endorphin, endothelin, enkephalin, epidermal growth factor, fertirelin, follicular gonadotropin releasing peptide, galanin, glucagon, gonadorelin, gonadotropin, goserelin, growth hormone releasing peptide, histrelin, insulin, leuprolide, LHRH, motilin, nafarelin, neurotensin, oxytocin, somatostatin, substance P, tumor necrosis factor, triptorelin, and vasopressin. Analogs, derivatives, antagonists, agonists and pharmaceutically acceptable salts of the above may also be used.

The peptide compounds useful in the formulations and methods of the present invention can be used in the form of a salt, preferably a pharmaceutically acceptable salt. Useful salts are known to those of skill in the art and include salts with inorganic acids, organic acids, inorganic bases or organic bases. Preferred salts are acetate salts.

Peptides and peptide compounds which are readily soluble in non-aqueous polar aprotic solvents are preferred for use in the present invention. One of skill in the art can easily determine which compounds will be useful on the basis of their solubility, i.e., the compound must be soluble in the particular non-aqueous polar aprotic solvent to at least an acceptable amount. Preferred solubilities are at least about 10% (w/w). Particularly preferred peptide compounds are LHRH-related compounds, including leuprolide and leuprolide acetate.

The proportion of peptide may vary depending on the compound, the condition to be treated, the solubility of the compound, the expected dose and the duration of administration. (See, for example, *The Pharmacological Basis of Therapeutics*, Gilman et al., 7th ed. (1985) and *Pharmaceutical Sciences*, Remington, 18th ed. (1990), the disclosures of which are incorporated herein by reference.) The concentration of peptide in high concentration formulations may range from at least about 10% (w/w) to the maximum solubility of the compound. A preferred range is from about 20 to about 60% (w/w). The currently more preferred range is from about 30 to about 50% (w/w) and a most preferred range is about 35 to about 45% (w/w).

Figure 7:
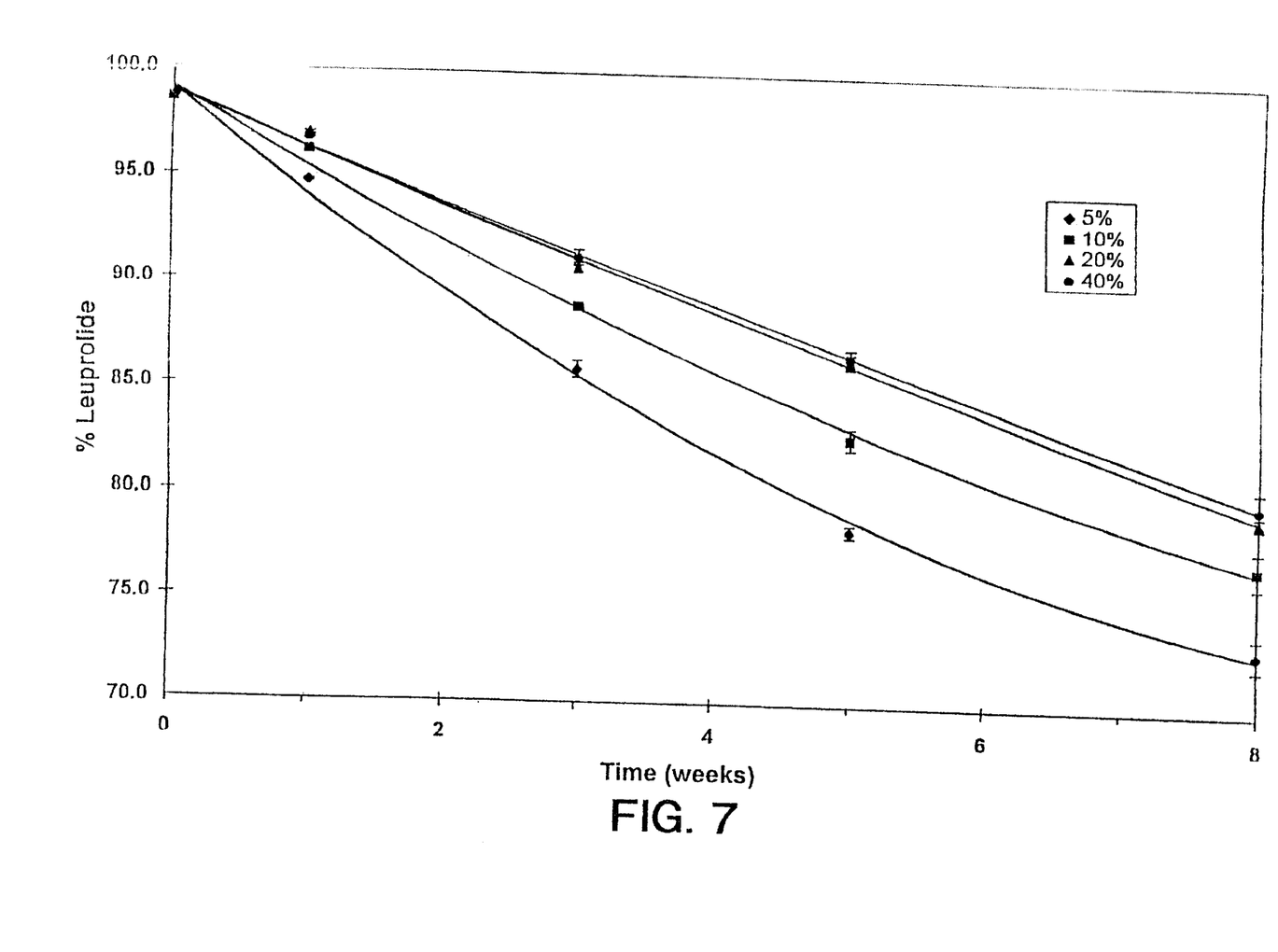
FIG. 7 illustrates that increasing the concentration of the peptide leuprolide in DMSO solution increased stability at 80° C.

It has unexpectedly been found that increasing the concentration of peptide that is dissolved in the non-aqueous polar aprotic solvent may increase the stability of the peptide formulation. For example, as seen in FIG. 7, when solutions of 5, 10, 20 and 40% leuprolide in DMSO were stored for 8 weeks at 80° C. with samples taken periodically and analyzed to determine the percentage of leuprolide remaining, formulations containing higher concentrations of leuprolide were more stable than formulations with lower concentrations of leuprolide.

Generally, the stable formulations of the present invention may be prepared by simply dissolving the desired amount, which may be a therapeutically effective amount, of the desired peptide compound in the selected non-aqueous polar aprotic solvent. Preferred polar aprotic solvents include DMSO and DMF.

Figure 8:
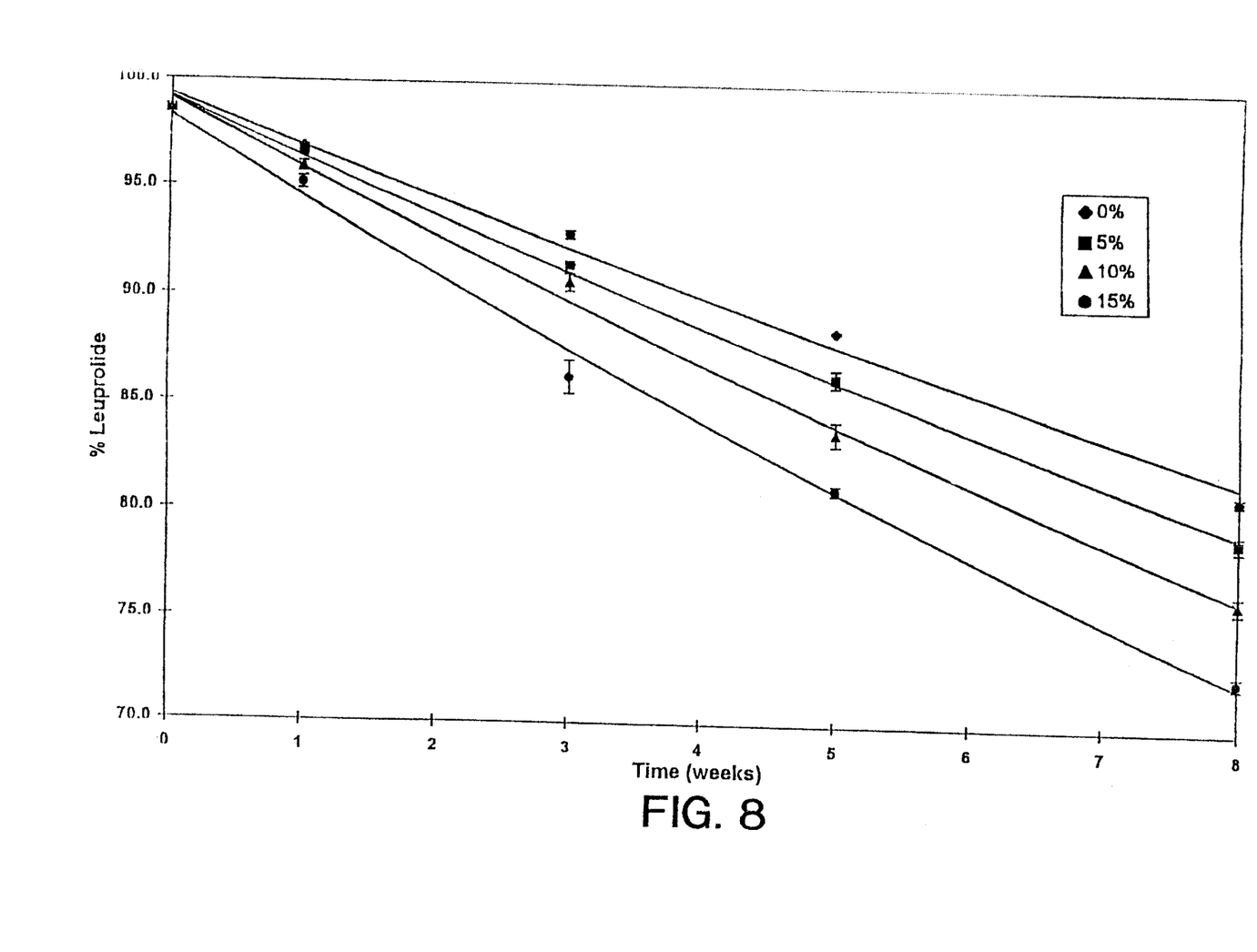
FIG. 8 illustrates that increasing the moisture content of 40% leuprolide-DMSO formulations resulted in decreased stability at 80° C.
Figure 9:
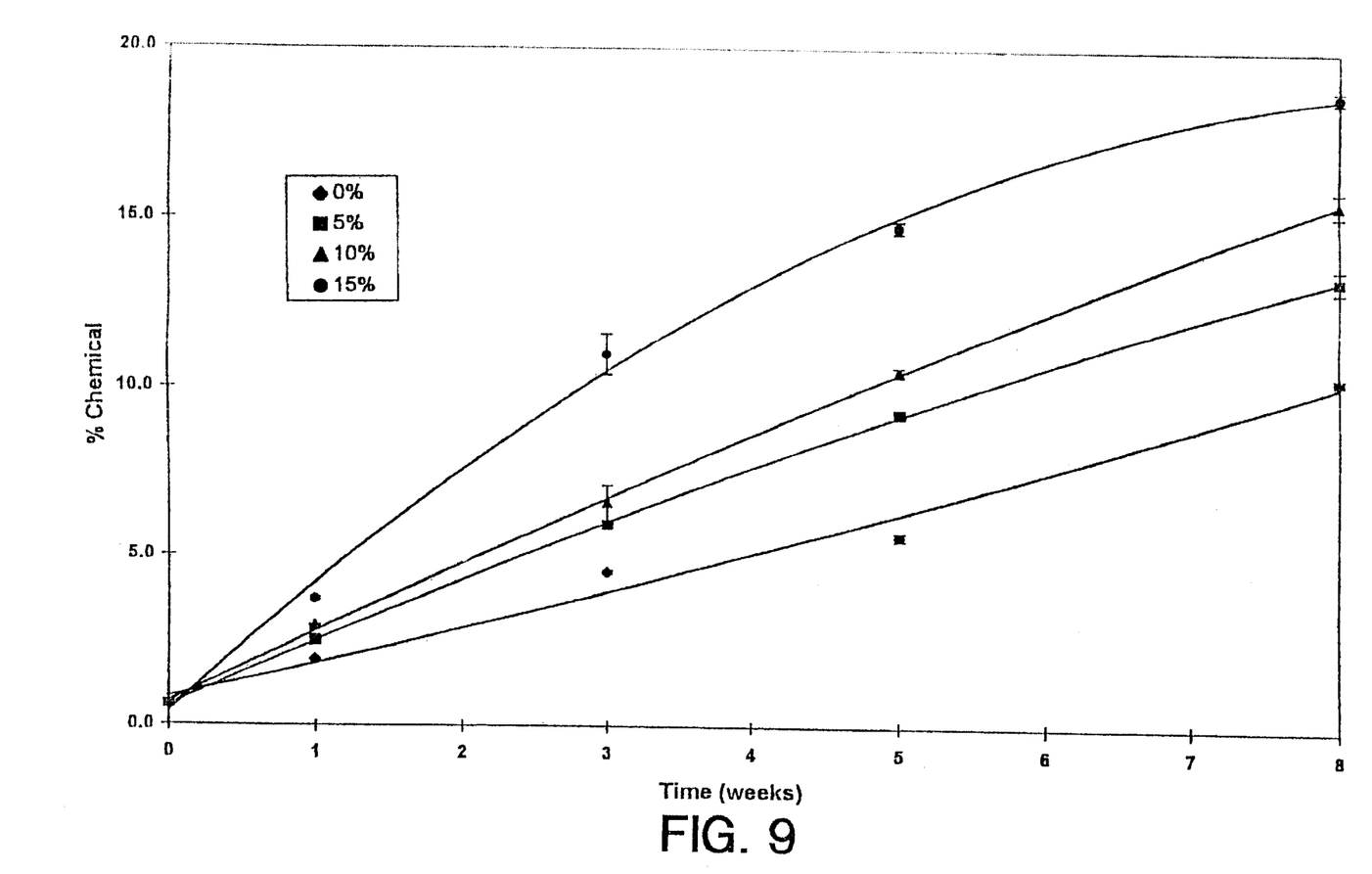
FIG. 9 illustrates that, in the formulations shown in FIG. 8, chemical degradation products increased with increasing moisture.

Increasing the water contained in the peptide formulations of the present invention increased peptide degradation as shown in FIG. 8. It appears that this increase may be due mainly to increasing chemical degradation products, with aggregation remaining relatively constant (FIG. 9).

It has also been found that non-aqueous protic solvents such as PEG, PG and PVP may optionally be added to the claimed formulations.

C. Methodology:

We have found that stable non-aqueous formulations of peptide compounds may be prepared by dissolving the peptide compound to be formulated in non-aqueous polar aprotic solvents.

We have tested these peptide compound formulations, specifically formulations of the LHRH-related compound leuprolide, for stability by subjecting them to accelerated aging at elevated temperature and measuring the chemical and physical stability of the formulations. Results of these studies (shown, for example, in Table II and FIGS. 1, 2, 4 and 6) demonstrate that these formulations were stable at conditions that approximate or exceed storage for one year at 37° C.

We have also tested peptide compound formulations prepared as described herein for stability after 2.5 megarad gamma irradiation. Results, shown in Table III, show that these formulations remained chemically and physically stable after such irradiation.

As shown in Table I, we have tested a wide variety of peptide formulations, specifically leuprolide, goserelin, LHRH, angiotensin I, bradykinin, calcitonin, enkephalin, insulin, neurotensin, substance P, trypsinogen and vasopressin, for stability by dissolving (or attempting to dissolve) them in the non-aqueous polar aprotic solvent DMSO, then subjecting them to accelerated aging at elevated temperatures. The stability of the formulations was measured. Results are presented in Table I as half-life at 37° C. assuming an $E_a$=22.2 kcal/mole. A wide range of the peptides tested were soluble in DMSO and remained stable under the test conditions. The solubility of a particular peptide in a particular non-aqueous polar aprotic solvent and the stability of the resulting solution are easily determined using routine procedures known to those of ordinary skill in the art.

TABLE I

Stability of Peptides Formulated in DMSO

| FORMULATION | HALF-LIFE* (Temperature) |
|---|---|
| 40% Leuprolide | 29.8 years (37° C.) |
| 40% Goserelin | 5.0 years (80° C.) |
| 20% LHRH | 8.2 years (65° C.) |
| 20% Angiotensin I | 4.2 years (65° C.) |
| 5% Angiotensin I | 4.1 months (50° C.) |
| 20% Bradykinin | 2.9 months (65° C.) |
| 40% Calcitonin | insoluble (80° C.) |
| 20% Calcitonin | 2.4 months (80° C.) |
| 5% Calcitonin | 100% stability at 2 months (50° C.) |
| 10% Enkephalin | 1.9 months (80° C.) |
| 5% Enkephalin | 2.6 months (50° C.) |
| 20% Insulin | insoluble gel (65° C.) |
| 5% Neurotensin | 5.0 months (50° C.) |
| 5% Substance P | 3.0 months (50° C.) |
| 40% Trypsinogen | insoluble crystal/gel (65° C./80° C.) |
| 20% Trypsinogen | insoluble gel (65° C.) |
| 5% Trypsinogen | 5.9 months (50° C.) |

TABLE I-continued

Stability of Peptides Formulated in DMSO

| FORMULATION | HALF-LIFE* (Temperature) |
|---|---|
| 40% Vasopressin | degraded (80° C.) |
| 20% Vasopressin | 11.8 days (65° C.) |

*Half-life at 37° C. assuming $E_a$ = 22.2 kcal/mole.

Formulations of 40% peptide in DMSO stored for six months at 37° C., 50° C., 65° C. and 80° C. showed non-linear Arrhenius kinetics as measured by overall loss of peptide from the solution, showing stability of these formulations at elevated temperatures. Analysis of data collected at 37° C. gave a $t_{90}$ of 14.4 months, indicating that stability at 37° C. is still very good.

Temperature appears to affect both the rate of degradation and the ratio of the degradation products of the formulations of the present invention. Studies of leuprolide-DMSO formulations have shown that at 65° C. and 80° C. oxidation appears to be the major chemical degradation pathway. Conversely, at 37° C. and 50° C. hydrolysis and isomerization appear to be the predominant degradation routes for these formulations.

We have also unexpectedly found that certain peptide formulations of the present invention are bacteriostatic (i.e., inhibit bacterial growth), bactericidal (i.e., cause the death of bacteria), and sporicidal (i.e., kill spores). In particular, leuprolide formulations of 50–400 mg/ml exhibited bacteriostatic, bactericidal and sporicidal activity. The stability of the samples was unaffected by spiking with bacteria, indicating that the enzymes released from the killed and lysed bacteria did not adversely affect the stability of the product. This demonstrates that these formulations were not conducive to enzymatic activity.

Some peptides, for example calcitonin and leuprolide, are known to be physically unstable, exhibiting aggregation, gelation and fibrillation when formulated in aqueous solution. Improving physical stability can increase bioavailability, alleviate sensitization and immune response, and allow for easier parenteral administration, including administration using implantable drug delivery systems.

It has unexpectedly been found that certain peptides, such as leuprolide, goserelin and calcitonin, formulated in the non-aqueous polar aprotic solvents of the present invention do not gel. No gelation was found even after 12 months at 37° C. This is apparently because non-aqueous polar aprotic solvents cause peptides to form a random coil/alpha helix conformation that does not refold into a beta sheet structure and, therefore, does not gel. Thus, these solvents have an anti-gellant effect.

A major aspect of the invention is that non-aqueous solutions containing peptide compounds in polar aprotic solvents are chemically and physically stable at high temperatures for long periods of time. Such formulations are stable even when high concentrations are used. Thus, these formulations are advantageous in that they may be shipped and stored at temperatures at or above room temperature for long periods of time. They are also suitable for use in implantable delivery devices.

DISCLOSURE OF EXAMPLES OF THE INVENTION

The following methods were used to perform the studies in the Examples that follow.

1. Preparing Leuprolide Acetate Solutions

Leuprolide acetate (obtained, for example, from Mallinckrodt, St. Louis, Mo.) was weighed and dissolved with stirring or centrifugation in vehicle (DMSO, DMF, DMSO/PEG, DMSO/PG, or DMSO/PVP) at the appropriate concentration. The term dry DMSO refers to DMSO formulations prepared in a low moisture environment (i.e., dry $N_2$ atmosphere).

Unless otherwise noted, leuprolide free base content was calculated from certificate of analysis potency values to be 37° C. free base. This was 40% leuprolide acetate, except as noted.

2. Preparation of Reservoirs

The reservoirs of implantable drug delivery devices (as disclosed in U.S. patent application Ser. No. 08/595,761, incorporated herein by reference) were filled with the appropriate leuprolide acetate solution. The formulation was filled into titanium or polymer reservoirs with a polymer plug blocking each end. The filled reservoir was then sealed in a polyfoil bag and placed in a stability testing oven.

It should be noted that the formulations in the reservoirs of these devices are completely isolated from the outside environment.

3. Reverse Phase-HPLC(RP-HPLC)

All stability samples were analyzed for leuprolide concentration and % peak area using a gradient elution reversed-phase HPLC assay with a refrigerated autosampler (4° C.) to minimize sample degradation. The chromatographic conditions used are listed below.

| Description | Parameter |
| --- | --- |
| Column | HaiSil C18, 4.6 × 250 mm, S/N 5103051 |
| Flow Rate | 0.8 mL min$^{-1}$ |
| Injection Volume | 20 μL |
| Detection | 210 nm |
| Leuprolide Retention Time | Between 25–30 minutes |
| Mobile Phase | A = 100 mM Sodium Phosphate, pH 3.0 |
| | B = 90% Acetonitrile/Water |

| Gradient | Minutes | 0 | 5 | 25 | 40 | 41 | 46 | 46.1 | 50 |
| --- | --- | --- | --- | --- | --- | --- | --- | --- | --- |
| | % B | 15 | 26.5 | 26.5 | 65 | 85 | 85 | 15 | 15 |

Leuprolide standards (in water) at 4 to 6 different concentration levels, typically between 0.1–1.2 mg/mL, were run along with the stability samples. The stability samples were bracketed by the standard sets, with no more than 40 samples in between the standard sets. All peaks between the void volume and 45 minutes of the run were integrated. The integrated peak areas for the leuprolide standards were plotted as a function of the concentration. The leuprolide concentrations for the stability samples were then calculated using linear regression. The % peak areas for the leuprolide peak, the sum of all the peaks eluting before leuprolide (labeled "others"), and the sum of all the peaks eluting after leuprolide (labeled "aggregates") were also recorded and plotted as a function of the sample timepoints.

4. Size Exclusion Chromatography (SEC)

Selected stability samples were analyzed for % peak area and molecular weights using an isocratic solution SEC assay with a refrigerated autosampler (4° C.). The chromatographic conditions used are listed below.

| Description | Parameter |
| --- | --- |
| Column | Pharmacia Peptide, HR 10/30, 10 × 300 mm |
| Flow Rate | 0.5 mL min$^{-1}$ |
| Injection Volume | 20 μL |
| Detection | 210 nm |
| Leuprolide Retention Time | Approximately 25 minutes |
| Mobile Phase | 100 mM Ammonium Phosphate, pH 2.0, 200 mM Sodium Chloride, 30% Acetonitrile |

The void volume and total volume for the size exclusion column was needed for the calculation of the molecular weights. The BioRad high molecular weight standard and 0.1% acetone were used to determine the void volume and total volume respectively. The retention times for the first peak in the BioRad standard and the acetone peak were recorded and converted to volume units using the equations below. Since these values are constant for a particular SEC column and HPLC system, the void and total volumes were redetermined whenever changes to the SEC column or HPLC system were made. A standard run was then made followed by the stability samples. The standard mixture contained approximately 0.2 mg/mL of the following peptides: Bursin (MW=449), WLFR peptide (MW=619), Angiotensin (MW=1181), GRF (MW=5108), and Cytochrome C (MW=12394). These standards were chosen because they bracketed leuprolide molecular weight and all had basic pI (9.8–11.0), similar to leuprolide.

The % peak areas were recorded for all the peaks. The molecular weights for the species separated were calculated using the equations below.

$V_s$=flow rate (mL/min)×sample peak retention time (min)

$V_o$=flow rate (mL/min)×void volume peak retention time (min)

$V_t$=flow rate (mL/min)×total volume peak retention time (min)

$$Kd = \frac{V_s - V_o}{V_t - V_o}$$

Where:

$V_s$=standard or sample volume $V_o$=void volume $V_t$=total volume $V_s$ was calculated to each peptide standard peak. Kd for each peptide standard was then calculated using the values for $V_t$ and $V_o$ determined earlier. The linear regression line from the plot of logMW vs. Kd$^{-1}$ was used to determine the molecular weights for each peak in the stability sample. The % peak areas for the stability samples were also recorded.

5. Instrumentation and Materials

The instrumentation and materials used for RP-HPLC and SEC were as follows:

Waters Millennium HPLC system consisting of 717 autosampler, 626 pump, 6000S controller, 900 photodiode array detector, and 414 refractive index detector (Waters Chromatography, Milford, Ma.)

HPLC vials, for 48-position and 96-position (Waters Chromatography, Milford, Ma.)

HaiSil C18, 120 A, 5 μm4.6 ×250 mm HPLC column (Higgins Analytical, Mountain View, Calif.)

Pharmacia Peptide, HR 10/30 SEC column (Pharmacia Biotech, Piscataway, N.J.)

The following examples are offered to illustrate this invention and are not meant to be construed in any way as limiting the scope of this invention.

EXAMPLE 1

Accelerated Stability Studies of Leuprolide Acetate Formulations

Formulations of 40% (w/w) leuprolide acetate (equivalent to about 37% leuprolide free base) in vehicle were prepared as described above and used to fill the reservoirs of implantable drug delivery devices, also as described above. All reservoirs were made of titanium.

The filled devices were subjected to accelerated aging by storing them at elevated temperatures (80° C.) for seven days in an oven (Precision Scientific or Thelco). This is equivalent to about 1.5 years at 37° C. or about four years at room temperature (25° C.).

The samples were analyzed using RP-HPLC and SEC as described above to determine the chemical and physical stability of the aged formulations.

Results, presented in Table II, demonstrate that these formulations were able to maintain the stability of the LHRH-related compound leuprolide. In each case, at least 65% leuprolide was retained.

TABLE II

Stability of Leuprolide Acetate Polar Aprotic Formulations After 7 Days at 80° C. in Titanium Reservoirs

| Formulation | % Leuprolide at Day 7 |
|---|---|
| 40% in DMSO | 92 |
| 40% in DMSO/PEG (50/50) | 90 |
| 40% in DMSO/PG (50/50) | 86 |
| 40% in DMSO/PVP (50/50) | 93 |
| 40% in DMF | 91 |
| 40% in dry DMSO | 89 |

EXAMPLE 2

Stability Studies of Irradiated Leuprolide Acetate Formulations

Formulations of 40% (w/w) leuprolide acetate in DMSO were prepared as described above and used to fill the reservoirs of drug delivery devices, also as described above. All reservoirs were made of titanium.

The filled devices were sent to Sterigenics (Tustin, Calif.) where they were subjected to 2.5 megarad gamma irradiation using Cobalt 60, 3-level "tote box" irradiation in Sterigenics' Tustin Main Cell. In Table III, the samples labeled "cold" were shipped and irradiated on dry ice. Samples were then subjected to accelerated aging as in Example 1. Samples were taken at day 0 and day 7, and analyzed using RP-HPLC and SEC as described above to determine the chemical and physical stability of the irradiated formulations.

Results, presented in Table III, demonstrate that these leuprolide acetate formulations were stable after irradiation. In every case, at least 65% leuprolide was retained, with low levels of aggregate formation.

TABLE III

Stability of 40% (w/w) Leuprolide Acetate Polar Aprotic Formulations After 2.5 Megarad Gamma Irradiation in Titanium Reservoirs

| | | % Leuprolide at | SEC | | | |
|---|---|---|---|---|---|---|
| | | | Day 0 | | Day 7 | |
| Formulation | Irradiation | Day 7 (RP-HPLC) | % monomer | % dimer/trimer | % monomer | % dimer/trimer |
| 40% in DMSO | Yes | 100 | 98.1 | 0.5 | 97.7 | 1.9 |
| 40% in DMSO | No | 90 | 100 | 0 | 98.5 | 1.1 |
| 40% in DMSO | Cold | 99 | 99.1 | 0.2 | 98.3 | 1.4 |
| 40% in DMSO | Yes | 95 | 99.1 | 0.8 | 95.3 | 2 |
| 40% in DMSO | No | N.D. | 100 | 0 | 106.1 | 0 |
| 40% in DMSO | Yes | 90 | 99.4 | 0.6 | 99.4 | 2.2 |
| 40% in DMSO | No | 100 | 100 | 0 | 104 | 1 |
| 40% in DMSO | Yes | 88 | 99.5 | 0.5 | 97.7 | 1.8 |
| 40% in DMSO | Yes | 83 | 99.5 | 0.5 | 91.7 | 1.5 |

EXAMPLE 3

Accelerated Long-Term Stability Studies of Leuprolide Acetate Formulations

Figure 1:
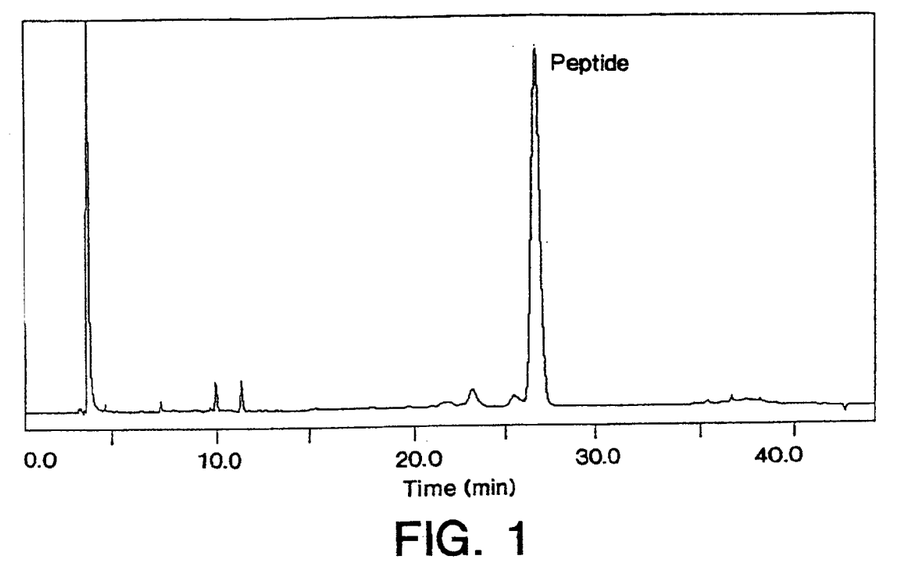
FIG. 1 illustrates the stability of 40% leuprolide acetate solution (w/w) in dimethylsulfoxide (methylsulfoxide or DMSO) after two months at 80° C. as measured by reverse phase HPLC (RP-HPLC).
Figure 2:
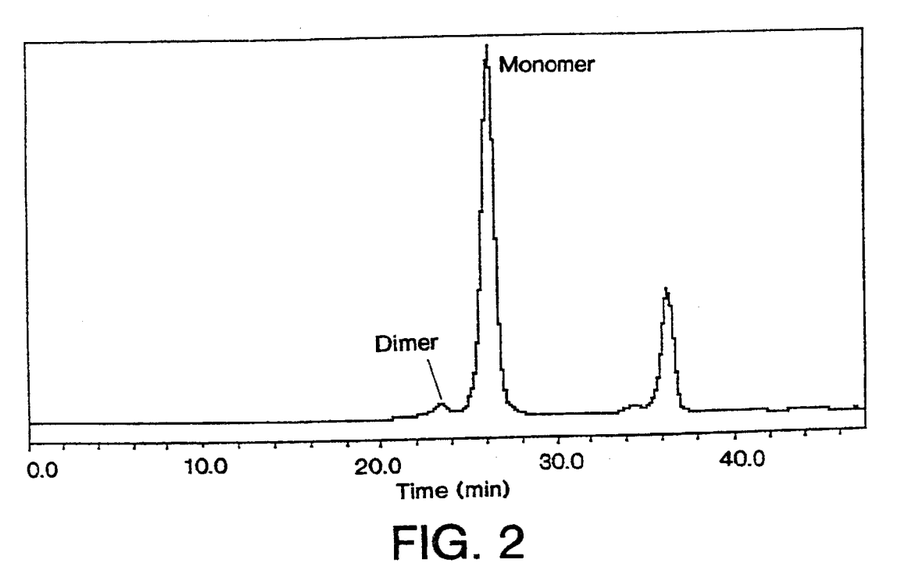

Solutions of 40% leuprolide acetate (w/w) in DMSO were prepared, loaded into reservoirs, stored for two months at 80° C. and analyzed as described above. Results, shown in FIGS. 1 (RP-HPLC) and 2 (SEC) show that 81.1% leuprolide was recovered, with only 14.6% chemical degradation and 5.1% physical aggregation.

Figure 4:
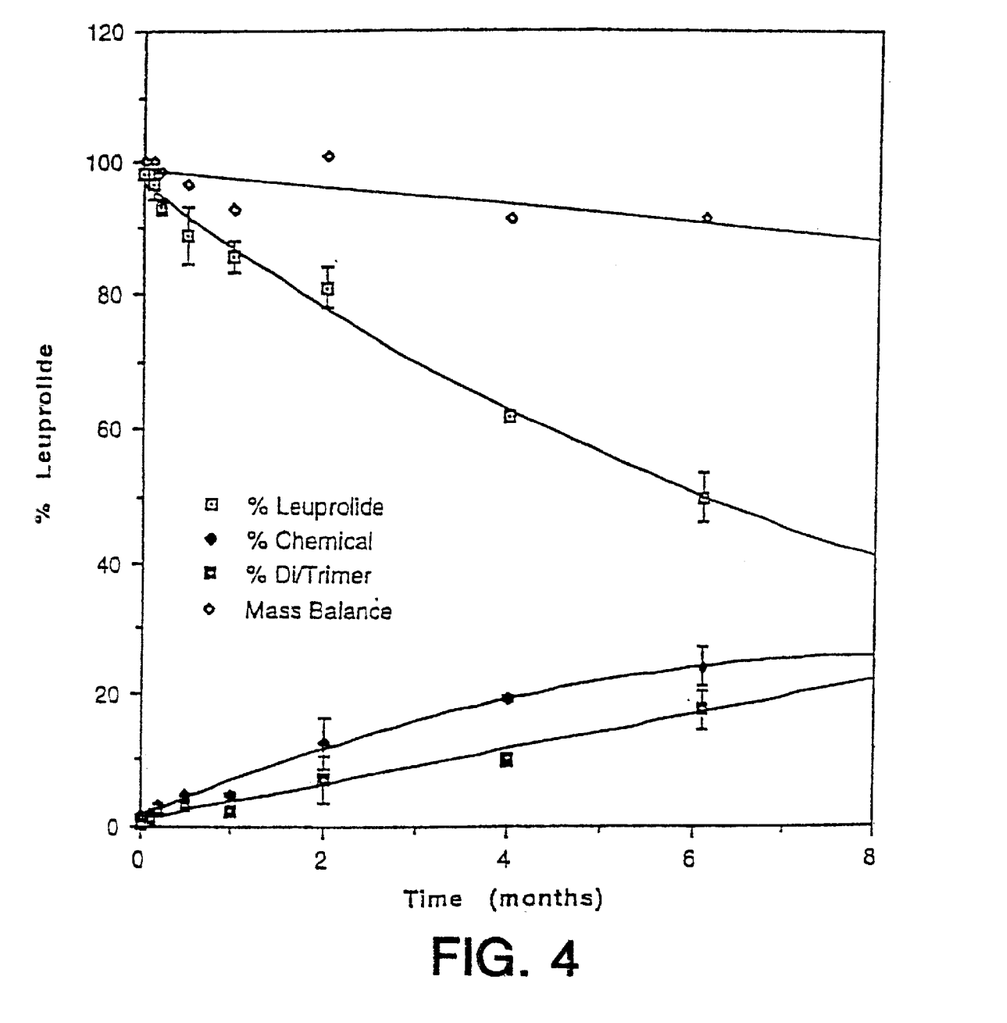
FIG. 4 illustrates the chemical and physical stability of a 40% leuprolide solution in DMSO after six months at 80° C.
Figure 5:
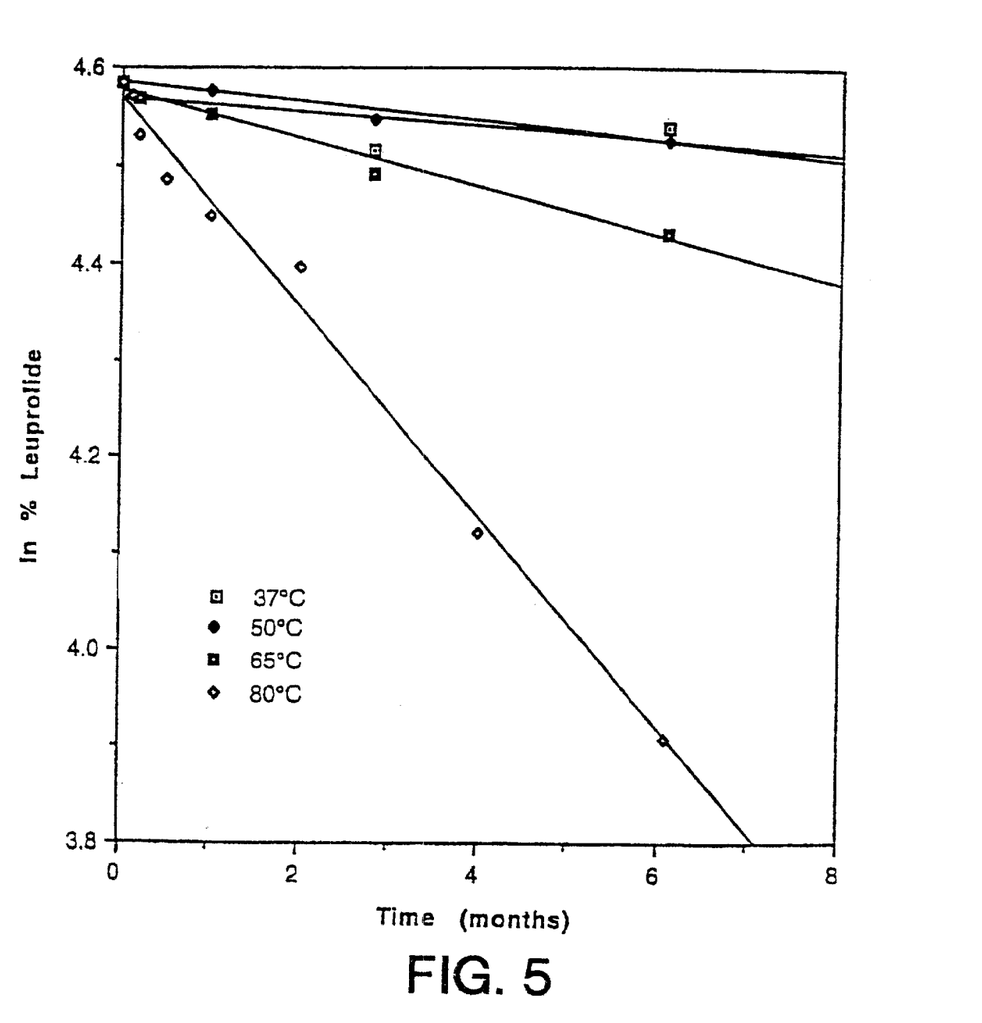
FIG. 5 illustrates the loss of leuprolide from a 40% leuprolide acetate solution in DMSO over a period of six months at 37° C., 50° C., 65° C. or 80° C.
Figure 6:
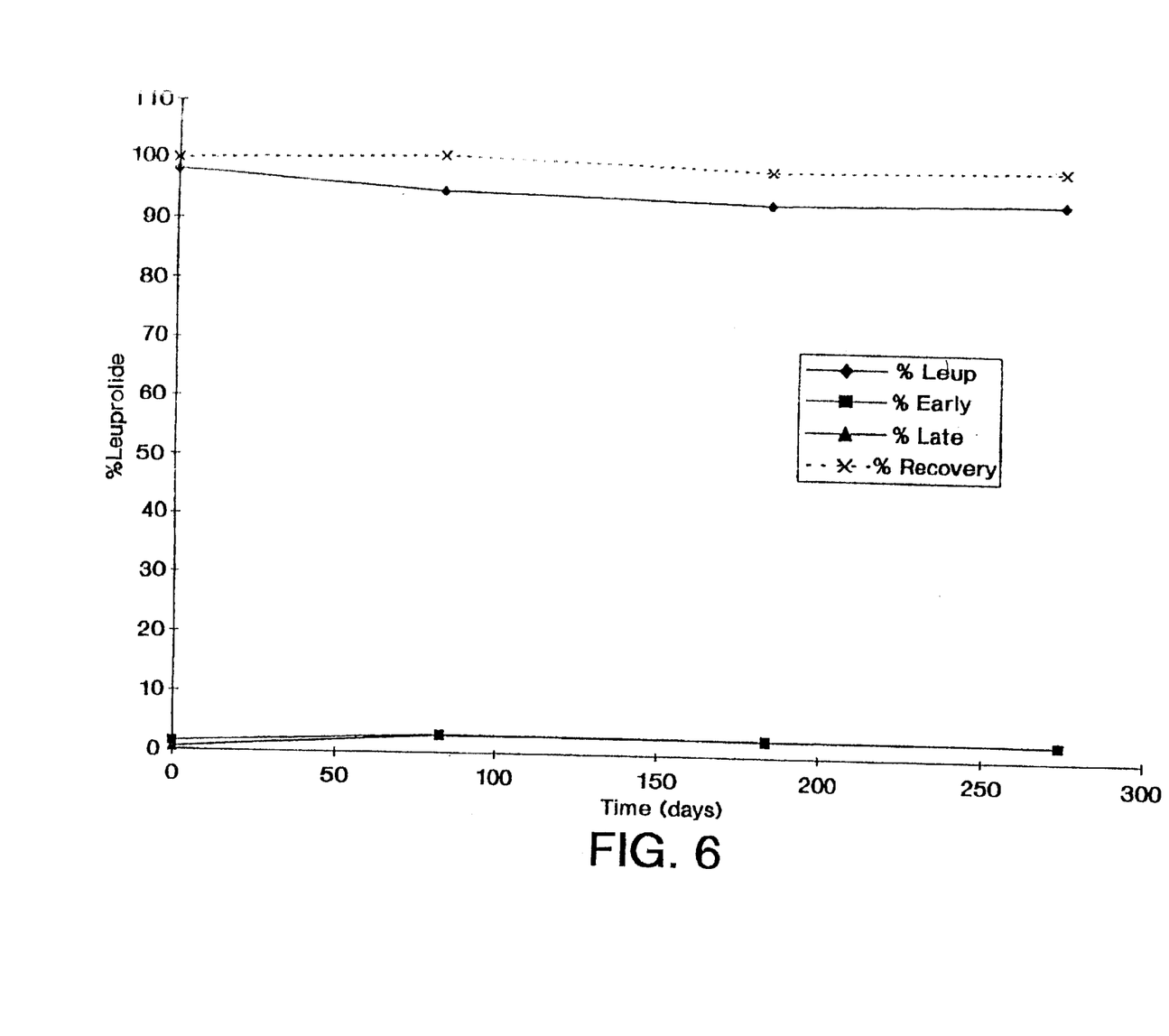
FIG. 6 illustrates the chemical stability of a 40% leuprolide acetate solution in DMSO over a period of nine months at 37° C.

Leuprolide acetate solutions were prepared, loaded, stored at 80° C. for six months and analyzed as described above. FIG. 4 is a plot of leuprolide, and its chemical and physical degradation products recovered over the six month time period, showing that we accounted for all the peptide material we started with and that these formulations showed good stability at 80° C. The sum of these three elements is also presented as mass balance. FIG. 5 is a plot of the natural log of these data, showing that these formulations exhibited linear kinetics over the entire temperature range tested.

The chemical stability of 40% leuprolide acetate solutions prepared and analyzed as described above is presented in FIG. 6. After nine months at 37° C. more than 90% (93.5%) leuprolide was present, with less than 5% (2.9%) chemical degradation products (shown as "early" in the figure) and less that 5% (2.3%) physical degradation products (shown as "late" and based on the RP-HPLC profile, but in good agreement with SEC) being formed.

Figure 3:
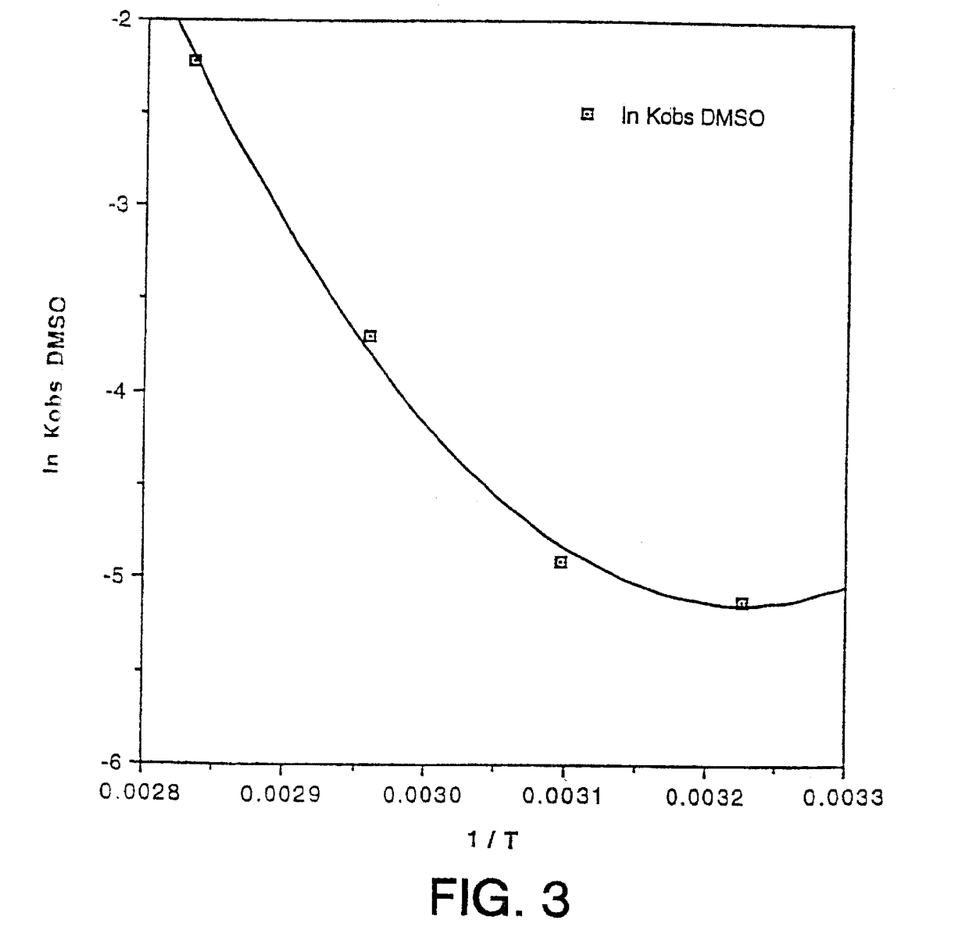
FIG. 3 presents the Arrhenius plot showing the loss of leuprolide from 40% solutions of leuprolide acetate in dimethylsulfoxide (DMSO).

Solutions of 40% leuprolide acetate (w/w) in DMSO were prepared, loaded into reservoirs, stored at 37° C., 50° C., 65° C. or 80° C. and analyzed using RP-HPLC as described above. Results were calculated as described in *Physical Pharmacy: Physical Chemical Principles in the Pharmaceutical Sciences*, 3rd ed., Martin et al., Chapter 14 (1983) and showed that loss of leuprolide from DMSO formulations was non-linear. The data are shown below and an Arrhenius plot is presented in FIG. 3.

Because Arrhenius plots of DMSO formulations stored at 80° C. showed that loss of leuprolide was non-linear, stability data collected at 37° C. was used to calculate a $t_{90}$ for these formulations of 14.4 months at 37° C.

| | DMSO | |
|---|---|---|
| ° C. | Kobs (months$^{-1}$) | t½(months) |
| 37 | 7.29 × 10$^{-3}$ | 95.1 |
| 50 | 9.74 × 10$^{-3}$ | 71.2 |
| 65 | 2.48 × 10$^{-2}$ | 27.9 |
| 80 | 0.108 | 6.4 |

$E_a$ = non-linear

EXAMPLE 4

Stability Studies of Leuprolide Acetate Formulations in DMSO/Water

Formulations of 40% leuprolide acetate (w/w) in DMSO, DMSO/water (95:5, 90:10, 70:30, 50:50, and 30:70) and water were prepared as described above and incubated for seven days at 80° C. Fourier Transfer Infrared Spectroscopy (FTIR) analysis was performed at day 0 and at day 7.

Results showed that the structural conformation of leuprolide changed very little after this accelerated aging for all the formulations tested. In general, peptide structure was predominantly random coil or a-helix in DMSO formulations, while peptide structure was predominantly β-sheet in water formulations.

Modification of the above-described modes of carrying out various embodiments of this invention will be apparent to those of skill in the art following the teachings of this invention as set forth herein. The examples described above are not limiting, but are merely exemplary of this invention, the scope of which is defined by the following claims.

What is claimed is:

1. A stable non-aqueous formulation of a peptide compound comprising:
   a) at least one peptide compound; and
   b) at least one polar aprotic solvent, wherein said polar aprotic solvent is selected from the group consisting of DMSO and DMF.

2. A stable non-aqueous formulation of a peptide compound comprising:
   a) at least one peptide compound; and
   b) at least one polar aprotic solvent, which is stable after irradiation.

3. A stable non-aqueous formulation of a peptide compound comprising:
   a) at least one peptide compound; and
   b) at least one polar aprotic solvent, which does not contain components containing added water.

4. A stable non-aqueous formulation of a peptide compound comprising:
   a) at least one peptide compound; and
   b) at least one polar aprotic solvent, which exhibits bacteriostatic, bactericidal or sporicidal activity without the use of a conventional bacteriostatic, bactericidal or sporicidal agent, wherein said peptide compound is an LHRH-related compound.

5. The formulation of claim 1 which comprises at least about 10% (w/w) peptide compound.

6. The formulation of claim 1 which comprises at least about 30% (w/w) peptide compound.

7. The formulation of claim 1 of which is stable at 80° C. for at least 2 months.

8. The formulation of claim 1 which is stable at 37° C. for at least 3 months.

9. The formulation of claim 1 which is stable at 37° C. for at least one year.

10. The formulation of claim 1 which is adapted for use in an implantable drug delivery device.

11. The formulation of claim 1 wherein said polar aprotic solvent provides an anti-gellant effect.

12. The formulation of claim 1 which is stable after irradiation.

13. The formulation of claim 1 wherein said peptide is an LHRH-related compound.

14. The formulation of claim 2 which comprises at least about 10% (w/w) peptide compound.

15. The formulation of claim 2 which comprises at least about 30% (w/w) peptide compound.

16. The formulation of claim 2 of which is stable at 80° C. for at least 2 months.

17. The formulation of claim 2 which is stable at 37° C. for at least 3 months.

18. The formulation of claim 2 which is stable at 37° C. for at least one year.

19. The formulation of claim 2 which is adapted for use in an implantable drug delivery device.

20. The formulation of claim 2 wherein said polar aprotic solvent is selected from the group consisting of DMSO and DMF.

21. The formulation of claim 2 wherein said polar aprotic solvent provides an anti-gellant effect.

22. The formulation of claim 2 wherein said peptide is an LHRH-related compound.

23. The formulation of claim 3 which comprises at least about 10% (w/w) peptide compound.

24. The formulation of claim 3 which comprises at least about 30% (w/w) peptide compound.

25. The formulation of claim 3 of which is stable at 80° C. for at least 2 months.

26. The formulation of claim 3 which is stable at 37° C. for at least 3 months.

27. The formulation of claim 3 which is stable at 37° C. for at least one year.

28. The formulation of claim 3 which is adapted for use in an implantable drug delivery device.

29. The formulation of claim 3 wherein said polar aprotic solvent is selected from the group consisting of DMSO and DMF.

30. The formulation of claim 3 wherein said polar aprotic solvent provides an anti-gellant effect.

31. The formulation of claim 3 which is stable after irradiation.

32. The formulation of claim 3 wherein said peptide is an LHRH-related compound.

33. The formulation of claim 4 which comprises at least about 10% (w/w) peptide compound.

34. The formulation of claim 4 which comprises at least about 30% (w/w) peptide compound.

35. The formulation of claim 4 of which is stable at 80° C. for at least 2 months.

36. The formulation of claim 4 which is stable at 37° C. for at least 3 months.

37. The formulation of claim 4 which is stable at 37° C. for at least one year.

38. The formulation of claim 4 which is adapted for use in an implantable drug delivery device.

39. The formulation of claim 4 wherein said polar aprotic solvent is selected from the group consisting of DMSO and DMF.

40. The formulation of claim 4 wherein said polar aprotic solvent provides an anti-gellant effect.

41. The formulation of claim 4 which is stable after irradiation.

* * * * *

UNITED STATES PATENT AND TRADEMARK OFFICE
CERTIFICATE OF CORRECTION

PATENT NO : 6,124,261
DATED : September 26, 2000
INVENTOR(S) : Cynthia L. Stevenson, et al.

It is certified that error appears in the above-identified patent and that said Letters Patent are hereby corrected as shown below:

Col. 2, line 16
  replace "of claim 1 of"
  with --of claim 1--.

Col. 2, line 34
  replace "of claim 2 of"
  with --of claim 2--.

Col. 2, line 53
  replace "of claim 3 of"
  with --of claim 3--.

Col. 1, line 7
  replace "of claim 4 of"
  with --of claim 4--.

Signed and Sealed this

Seventeenth Day of April, 2001

Attest:

NICHOLAS P. GODICI

*Attesting Officer*     *Acting Director of the United States Patent and Trademark Office*